(12) United States Patent
Hornung et al.

(10) Patent No.: US 8,658,414 B2
(45) Date of Patent: Feb. 25, 2014

(54) BIOMASS PROCESSING

(75) Inventors: Andreas Hornung, Birmingham (GB); Andreas Apfelbacher, Birmingham (GB)

(73) Assignee: Aston University, Birmingham (GB)

( * ) Notice: Subject to any disclaimer, the term of this patent is extended or adjusted under 35 U.S.C. 154(b) by 624 days.

(21) Appl. No.: 12/992,647

(22) PCT Filed: May 13, 2009

(86) PCT No.: PCT/GB2009/001205
§ 371 (c)(1), (2), (4) Date: Nov. 15, 2010

(87) PCT Pub. No.: WO2009/138746
PCT Pub. Date: Nov. 19, 2009

(65) Prior Publication Data
US 2011/0070628 A1    Mar. 24, 2011

(30) Foreign Application Priority Data

May 14, 2008    (GB) .................................. 0808740.5

(51) Int. Cl.
*C12M 1/00* (2006.01)
*C12M 3/00* (2006.01)
*C12N 1/12* (2006.01)

(52) U.S. Cl.
USPC .................. 435/257.1; 435/283.1; 435/289.1

(58) Field of Classification Search
None
See application file for complete search history.

(56) References Cited

U.S. PATENT DOCUMENTS

| | | |
|---|---|---|
| 6,477,841 B1 | 11/2002 | Yantovsky |
| 2004/0144338 A1 | 7/2004 | Goldman |
| 2008/0182298 A1 | 7/2008 | Day |

FOREIGN PATENT DOCUMENTS

| | | |
|---|---|---|
| DE | 102007018875 | 4/2007 |
| DE | 102007053661 | 11/2007 |
| GB | 2254858 | 10/1992 |
| GB | 2339576 | 2/2000 |
| GB | 2339576 | 11/2002 |
| GB | 2008/020167 | 2/2008 |
| JP | 3154616 | 7/1991 |
| JP | 3169324 | 7/1991 |
| JP | 2006191876 | 7/2006 |
| WO | 02/50484 | 6/2002 |
| WO | 2004/037747 | 5/2004 |
| WO | 2004/072207 | 8/2004 |
| WO | 2007/020167 | 2/2007 |
| WO | 2007/027633 | 3/2007 |
| WO | 2007/144441 | 12/2007 |
| WO | 2008/020167 | 2/2008 |

OTHER PUBLICATIONS

International Search Report and Written Opinion from PCT/GB09/001205 dated Oct. 30, 2009.
Bridgwater, A.V. et al., "An overview of fast pyrolysis of biomass," Organic Geochemistry, vol. 30, 1999, pp. 1479-1493.
Bridgwater, A.V. et al., "Renewable fuels and chemicals by thermal processing of biomass," Chemical Engineering Journal, vol. 91, 2003, pp. 87-102.
Chisti, Yusuf, "Biodiesel from microalgae," Biotechnology Advances, vol. 25, 2007, pp. 294-306.
www.algaelink.com, at May 8, 2008.
ISR and WOISA for PCT/GB2009/001205, 2009.

*Primary Examiner* — Debbie K Ware
(74) *Attorney, Agent, or Firm* — Alston & Bird LLP

(57) ABSTRACT

A biomass processing system is disclosed, with an algae biomass growth container and a pyrolysis reactor for pyrolysis processing of the algae biomass. A conveying apparatus links the pyrolysis reactor and the biomass growth container for conveying at least part of at least one of the pyrolysis products from the reactor to the biomass growth container for promoting algae biomass growth. The pyrolysis product is a nutrient-rich aqueous phase produced directly or indirectly through pyrolysis processing to the biomass growth container, e.g. an aqueous phase derived from the vapor products of the pyrolysis, or a char wash obtained by washing the char product of the pyrolysis.

10 Claims, 1 Drawing Sheet

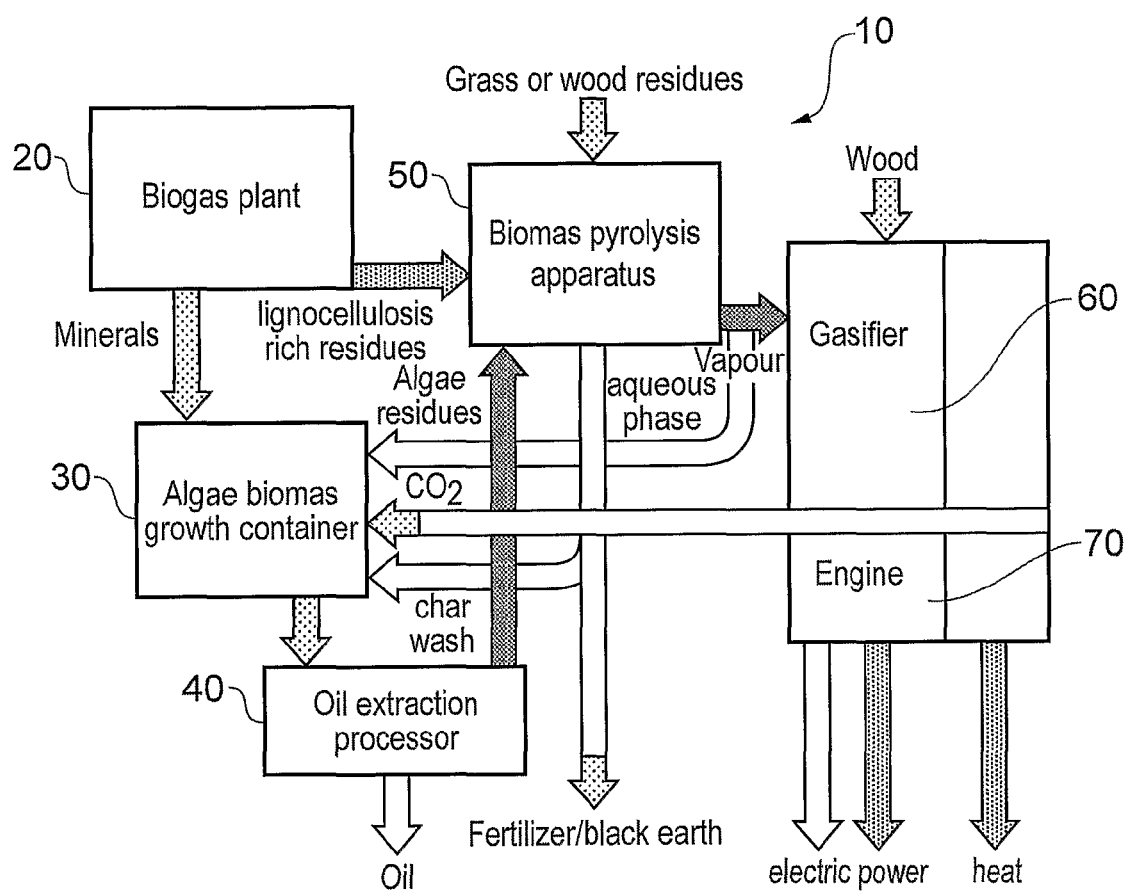

BIOMASS PROCESSING

CROSS REFERENCE TO RELATED APPLICATIONS

The present application is the U.S. national phase entry of PCT/GB09/001,205 with an international filing date of May 13, 2009, which claims the benefit of British Patent Application No. 0808740.5, filed on May 14, 2008, the entire disclosures of which are incorporated herein by reference.

BACKGROUND TO THE INVENTION

1. Field of the Invention

The present invention relates to biomass processing. It has particular, but not exclusive, application in the field of pyrolysis and/or gasification of algae biomass.

2. Related Art

Biomass pyrolysis is the thermal decomposition of biomass (e.g. plant material such as wood, wood bark, grasses, straw and algae) substantially in the absence of oxygen. Biomass is typically a mixture of hemicellulose, cellulose, lignin and small amounts of other organics.

The heating temperature and vapour residence times determine the proportion of gas, liquid and char produced by pyrolysis. For example, fast pyrolysis operates at moderate temperatures of 350 to 500° C. and short vapour residence times of less than two seconds to yield up to 75 wt. % liquid product on dry feed basis (A. V. Bridgwater, D. Meier, D. Radlein, "An overview of fast pyrolysis of biomass", Organic Geochemistry, 1999, 30, 1479-1493, incorporated herein by reference).

Dried algae mass is a useful source of biomass. Algae has a high biomass production rate per unit of hectare. Typically, 1.9 tons of dry algal biomass may be produced per day per hectare compared to 60 to 70 tons of grass per hectare per year (www.algaelink.com, accessed 8 May 2008).

Algae may be grown in ponds or bioreactors. To achieve fast growth rates, algae should be provided with carbon dioxide at a higher concentration than atmospheric carbon dioxide. Light and carbon dioxide are critical for photosynthesis, which allows the algae to grow. Nutrients are also required as rapid growth depletes any existing nutrient sources. Furthermore, for optimal growth, algae should be kept in the temperature range of 20 to 25° C.

WO 2007/144441 discloses a system of cultivating phytoplankton using solar or artificial light. The phytoplankton are harvested and useful chemical compounds are extracted.

U.S. Pat. No. 6,477,841 discloses a system for growing macroalgae in a body of water using solar energy. The macroalgae are harvested and combusted in a fluidized bed combustion chamber in an artificial atmosphere of oxygen and carbon dioxide.

SUMMARY OF THE INVENTION

The inventors have realised that an efficient process for the pyrolysis of biomass may be provided by linking a pyrolysis apparatus with a biomass growth container, in which at least part of the products of the pyrolysis may be used to promote biomass growth.

Accordingly, in a first preferred aspect, the present invention provides a biomass processing system having:
an algae biomass growth container;
a biomass pyrolysis apparatus for pyrolysis processing of biomass derived, at least in part, from the algae biomass growth container to produce pyrolysis products; and
a pyrolysis product conveying apparatus linking the biomass pyrolysis apparatus and the biomass growth container for conveying at least part of at least one of said pyrolysis products from the biomass pyrolysis apparatus to the biomass growth container for promoting algae biomass growth.

In a second preferred aspect, the present invention provides a biomass processing system having:
an algae biomass growth container;
a biomass pyrolysis apparatus for pyrolysis processing of biomass derived, at least in part, from the algae biomass growth container to produce pyrolysis products;
a gasifier for gasifying at least part of said pyrolysis products to produce gasification products; and
a gasification product conveying apparatus linking the gasifier and the biomass growth container for conveying at least part of at least one of said gasification products from the gasifier to the algae biomass growth container for promoting algae biomass growth.

In a third preferred aspect, the present invention provides a biomass processing system having:
an algae biomass growth container;
a biomass pyrolysis apparatus for pyrolysis processing of biomass derived, at least in part, from the algae biomass growth container to produce pyrolysis products;
a gasifier for gasifying at least part of said pyrolysis products to produce gasification products;
an engine operable by combusting at least one of said pyrolysis or gasification products to produce power and combustion products; and
a combustion product conveying apparatus linking said engine and the biomass growth container for conveying at least part of at least one of said combustion products from the engine to the algae biomass growth container for promoting algae biomass growth.

In a fourth preferred aspect, the present invention provides a method of biomass processing including the steps:
growing algae biomass in an algae biomass growth container for pyrolysis in the biomass pyrolysis apparatus;
removing algae biomass grown in said algae biomass growth container;
pyrolysing the algae biomass in a biomass pyrolysis apparatus to produce pyrolysis products; and
conveying with a pyrolysis product conveying apparatus at least part of at least one of said pyrolysis products from the biomass pyrolysis apparatus to the algae biomass growth container to promote algae biomass growth.

In a fifth preferred aspect, the present invention provides a method of biomass processing including the steps:
growing algae biomass in an algae biomass growth container for pyrolysis in a biomass pyrolysis apparatus;
removing algae biomass grown in said algae biomass growth container;
pyrolysing the algae biomass in said biomass pyrolysis apparatus to produce pyrolysis products
conveying at least part of at least one of said pyrolysis products to a gasifier for gasification;
gasifying the pyrolysis product in the gasifier to produce gasification products; and
conveying with a gasification product conveying apparatus at least part of at least one of said gasification products from the biomass pyrolysis apparatus to the algae biomass growth container to promote algae biomass growth.

In a sixth preferred aspect, the present invention provides a method of biomass processing including the steps:
- growing algae biomass in an algae biomass growth container for pyrolysis in a biomass pyrolysis apparatus;
- removing algae biomass grown in said algae biomass growth container;
- pyrolysing the algae biomass in said biomass pyrolysis apparatus to produce pyrolysis products;
- conveying at least part of at least one pyrolysis product to a gasifier for gasification;
- gasifying the pyrolysis product in the gasifier to produce gasification products;
- conveying at least part of at least one gasification product to an engine operable by combusting at least one of said pyrolysis or gasification products to produce power and combustion products;
- combusting the pyrolysis or gasification product in the engine to produce power and combustion products; and
- conveying with a combustion product conveying apparatus at least part of at least one of said combustion products from the engine to the algae biomass growth container to promote algae biomass growth.

The following preferred and/or optional features are applicable to any aspect of the invention, singly or in any combination, unless the context demands otherwise.

It is preferable that the pyrolysis product conveying apparatus conveys at least one of: heat, carbon dioxide, ash, water, char and aqueous phase of liquid pyrolysis product from the biomass pyrolysis apparatus to the algae biomass growth container.

It is preferable that the biomass processing system includes a gasifier for receiving at least part of at least one of said pyrolysis products to produce gasification products.

It is preferable that the biomass processing system includes a gasification product conveying apparatus linking the gasifier to the algae biomass growth container for conveying at least part of at least one of said gasification products from the gasifier to the algae biomass growth container to promote algae biomass growth.

It is preferable that the gasification product conveying apparatus conveys at least one of: heat, carbon dioxide, ash, water, ammonia, hydrogen sulphide and char from the gasifier to the algae biomass growth container.

It is preferable that the biomass processing system includes an engine operable by combusting at least one of said pyrolysis or gasification products to produce power and combustion products.

It is preferable that the biomass processing system further includes a combustion product conveying apparatus linking said engine to the algae biomass growth container for conveying at least part of at least one of the combustion products from the engine to the algae biomass growth container to promote algae biomass growth.

It is preferable that the combustion product conveying apparatus conveys at least one of: heat, carbon dioxide, ash, water and char from the engine to the algae biomass growth container.

Preferably the char contains at least 5% ash (by weight). Preferably, the ash content of the char is not more than 50% (by weight). Preferably, the char includes a carbon:oxygen ratio of at least 4:1 (by number of atoms). It is preferable that the char produced from the biomass pyrolysis apparatus is washed with water to produce a char residue solid and an aqueous nutrient solution, and wherein at least one of the char residue solid or the aqueous nutrient solution is conveyed to the algae biomass growth container for promoting algae growth.

It is preferable that the biomass processing system includes a biogas plant for providing at least a part of the biomass processing system with at least one biogas plant product.

It is preferable that the biogas plant produces an aqueous nutrient solution for conveying to the algae biomass growth container to promote algae growth.

It is preferable that the biogas plant produces a solid biogas plant residue for conveying to the biomass pyrolysis apparatus for pyrolysing.

It is preferable that, in use, a portion of the biomass supplied to the biomass pyrolysis apparatus is biomass grown elsewhere than in the algae biomass growth container. Preferably, this other biomass is not algae-derived biomass. Most preferably, it is agricultural- or forestry-derived biomass.

The algae biomass of the algae biomass growth container may supply the pyrolysis apparatus with at least part of the feedstock to generate pyrolysis products. At least one of the pyrolysis products may then be conveyed to the algae biomass growth container. Therefore, a cycle between a biomass pyrolysis apparatus and a biomass growth container may be established. In this system, at least part of at least one product of the biomass pyrolysis apparatus is recycled in order to reduce the cost and increase the efficiency of growing algae biomass. This leads to the formation of pyrolysis products in a cost-efficient and environmentally sound process.

Biomass feedstock in the form of dried algae may be processed by a biomass pyrolysis apparatus. The biomass pyrolysis apparatus has, at least, a pyrolysis reactor. There are many types of pyrolysis reactors known in the art. For example, see A. V. Bridgwater, "Renewable fuels and chemicals by thermal processing of biomass", *Chemical Engineering Journal*, 2003, 91, 87-102, and WO 02/50484, both of which are incorporated herein by reference.

It is preferable that the conditions for intermediate pyrolysis are used in the pyrolysis reactor of the biomass pyrolysis apparatus. Example conditions for intermediate pyrolysis may include a low to moderate reaction temperatures of 300 to 500° C., may include residence feedstock times of 0.5 to 25 minutes and may include moderate hot vapour residence times of 2 to 15 seconds.

The products of intermediate pyrolysis may be produced in the approximate ratios of 40-60:15-25:20-30% by weight of liquid (vapour):gas:solid char.

The liquid product of pyrolysis may be cooled to yield a bio-oil comprising a low energy aqueous phase and high energy oily phase. The bio-oil, typically, has a heating value of 18 MJ/kg, and may be used as biodiesel or stored to be processed at a later date. The aqueous phase product may contain nutrients. If separated from the oily phase, the aqueous phase product may supply the biomass growth container with water and nutrients.

The biomass processing system may include gasifier, which optionally forms all or part of the biomass pyrolysing apparatus. Gasification and types of gasification are summarised in A. V. Bridgwater, Renewable fuels and chemicals by thermal processing of biomass, *Chemical Engineering Journal*, 2003, 91, 87-102, which is incorporated herein by reference.

Preferably, the liquid product of pyrolysis is not cooled but is conveyed to the gasifier as a vapour. The gasifier typically heats the vapour to higher temperatures of 800 to 1400° C., typically around 1200 to 1400° C., in order to form synthesis gas or syngas.

The gas product of pyrolysis typically includes a mixture of CO, $H_2$ and low molecular weight hydrocarbons. This gas may be stored for future use or further processed either on-site or remotely.

The gas product of pyrolysis may also be conveyed with the vapours into the gasifier to process the gas product of pyrolysis. The gas product of the gasification process may include ammonia and/or $H_2S$. If the gas product of pyrolysis or gasification is combusted, e.g. in an engine, the resultant exhaust gas typically includes carbon dioxide, $NO_x$ and/or $SO_2$. These components of the exhaust gas may provide useful nutrients for algae growth.

It is preferable to convey the gas and liquid vapour products of pyrolysis to the gasifier. High ash biomass is not typically used in gasifiers to produce syngas. However, by coupling a pyrolyser with a gasifier, high ash biomass, such as algae, may be pyrolysed in the pyrolysis reactor to form products of pyrolysis. These products may then be gasified in the gasifier to yield syngas and other gasification products. The system allows processing of high ash biomass to form syngas.

Syngas from the gasifier may be stored, purified, conveyed to hydrogen fuel cell devices or conveyed to a bio-engine for combustion. Combustion of the syngas in the bio-engine produces electrical and thermal energy. The combustion also produces carbon dioxide, $NO_x$, $SO_2$ and water combustion products. At least part of at least one of said combustion products may be conveyed to the algae biomass growth container.

The algae growth container may be a pond or reservoir. The container may optionally include a sealed canopy to prevent the escape of gaseous products supplied to or derived from the algae. Alternatively, the algae growth container may comprise a tube or an array of tubes fully or partially filled with water. For typical examples of suitable growth containers see www.algaelink.com (accessed 8 May 2008) and www.varianaqua.com (accessed 12 May 2008).

The algae growth container is typically exposed to sunlight for promoting algae growth. The pyrolysis, gasification and/or combustion products conveyed to the algae biomass growth container may be controllably delivered into the biomass growth container.

When gaseous products of pyrolysis, gasification or combustion are conveyed to the algae biomass growth container, the gas levels in the container may be monitored. By providing the container with carbon dioxide, which is subsequently absorbed during algae growth, the amount of carbon dioxide released into the atmosphere is reduced. Since at least some exhaust gas is recycled within the biomass processing system, there may be no need to provide the biomass with carbon dioxide sourced separately and additional to atmospheric levels. At the same time, emissions of harmful greenhouse gases are reduced. When full cycling of carbon dioxide is performed in this way, the process is carbon neutral.

Char produced from the pyrolysis reactor may be used, at least in part, as a fuel source. It may also be used, at least in part, as a fertiliser at biomass growth sites. Char mixed with sand and/or soil is termed 'black earth', and is an effective way to sequester carbon. Instead of being released into the atmosphere, the carbon in black earth is slowly absorbed by the soil. In addition, the black earth is a good fertilizer for use on biomass growth areas. Returning the carbon to the soil in this way also does not significant quantities of methane, which is an extremely potent greenhouse gas.

Further products of the biomass pyrolysis apparatus may be conveyed to the biomass growth container for promoting growth of algae biomass.

It is preferable to wash at least part of the char produced by the biomass pyrolysis apparatus with water to yield an aqueous wash solution and a solid purified residue char. The aqueous wash solution contains nutrients. The solution may contain one following nutrients: potassium, phosphates, nitrates and silica. The phosphates may be present up to a 9:1 phosphate to nitrate ratio.

The aqueous nutrient solution may be supplied to the biomass growth container. The nutrients promote growth of the biomass. The use of the aqueous nutrient solution reduces the need for the use of fertilisers, thus reducing production costs. For algae production, it is considered suitable to provide a relatively high proportion of phosphorus-based nutrients compared with nitrogen-based nutrients (around eight parts phosphorus-based nutrients to one part nitrogen-based nutrients). The aqueous wash solution is typically rich in phosphorus-based nutrients. Nitrogen-based fertilizer may be added separately.

The solid residue from the aqueous wash of the char produced from the biomass pyrolysis apparatus contains carbon in a form suitable for sequestering and may contain mineral nutrients. The solid residue may be used to promote growth of biomass elsewhere than in the algae biomass growth container. The release of carbon into soil may be tailored by particle size. It is preferable that the solid residue has an average particle size by weight greater than 0.3 mm. It is preferable for the particle size by weight to be 0.4 to 10 mm. However, the material may be brittle, and so larger particle sizes may break down into smaller particle sizes with application of external force.

The biomass pyrolysis apparatus typically produces water as a pyrolysis product. The water may be condensed from one of the processes of the biomass pyrolysis apparatus, may contain at least one further product of the biomass pyrolysis apparatus and/or may be separated from another product of the biomass pyrolysis apparatus. At least part of the water may be supplied to the biomass growth container as a resource for the biomass growth. As the algae are grown in water, a ready supply and turnover of water is also useful for reducing stagnation.

The biomass processing system may produce excess heat either as a pyrolysis product or using one or more of the pyrolysis products as a fuel for combustion. At least part of the heat may be supplied to the biomass growth container. Algae grow optimally in the temperature range of 20 to 25° C. It is often hard to maintain these temperatures throughout the year at a fixed growth site without additional heating. By using at least part of the excess heat of the biomass processing system, the energy costs of the algae growth are reduced, and harvesting may easily be performed even during winter months.

The biomass is harvested to for pyrolysis in the pyrolysis reactor. The algae may optionally contain useful oils that may be extracted at this stage. Extraction techniques are known and may include drying and squeezing of the algae. Oil content ranges from 15 to 77% of algae dry weight. Chisti, Y., 2007, "Biodiesel from Microalgae", *Biotechnology Advances*, 25, 294-306 is incorporated herein by reference. The algae residue after oil extraction may be used in the pyrolysis reactor.

In pyrolysis, it is advantageous to use biomass of less than 25% water by weight. It is more preferable to use biomass of less than 10% water by weight. Thus, there is preferably a step of drying the algae after harvesting.

At least part of the excess heat from the biomass processing system may be used to dry the biomass. For example, at least part of the char may be combusted to heat and dry the algae. At least part of the water from the drying of the algae may be collected and conveyed to the algae growth container.

Once the algae biomass is dried, it may be charged into the biomass pyrolysis apparatus. This completes the cyclical process of the biomass processing system, and begins a further cycle.

The biomass pyrolysis apparatus optionally may include or be linked to a biogas plant. Typical biogas plants anaerobically digest biomass to produce methane as a biogas product. See www.schmack-biogas.com and www.nawaro.ag (both accessed 12 May 2008). Typically, the biomass is digested by fermentation with microbes in water.

Other biogas plant products include carbon dioxide and water rich with nutrients, which may, at least in part, be conveyed to the algae biomass growth container. A further product of the biogas plant is the solid residue of the biomass after digestion. The solid residue is typically high in lignocellulose content. At least part of the solid residue biogas plant product may be conveyed to the pyrolysis reactor for pyrolysis.

The biomass processing system may also be provided with biomass grown elsewhere than in the biomass growth container (Biomass A) in addition to the biomass from the algae biomass growth container (Biomass B).

Biomass A may be grown in atmospheric air. During growth of Biomass A, carbon dioxide is removed from the atmosphere for use in photosynthesis. On entering the biomass processing system, the same quantity of carbon dioxide is not released necessarily into the atmosphere from the processing of Biomass A, since at least part of the carbon or carbon dioxide from Biomass A is conveyed to the biomass growth container. Provided that at least part of the char from the biomass pyrolysis is sequestered, e.g. added to the soil to promote black earth, the overall process may be 'carbon negative'.

A further advantageous effect of the invention is that it may be used to produce a non-wood-based biochar which itself is low in nutrients and/or ash. Such a biochar may be comparable in properties and/or composition to biochar from wood, but can be generated from low grade, lignin rich materials which are comparatively cheap compared to wood biomass. The material used may be algae. The process used may include a pyrolysis step. This constitutes a further aspect of the present invention, which may be combined with any other aspect of the present invention.

BRIEF DESCRIPTION OF THE DRAWINGS

A preferred embodiment of the invention will now be described, by way of example, with reference to the drawing (FIG. 1), which shows a biomass processing system according to an embodiment of the invention, including a biogas plant, an algae growth container, a pyrolyser and a gasifier.

DETAILED DESCRIPTION OF THE PREFERRED EMBODIMENT AND FURTHER PREFERRED AND/OR OPTIONAL FEATURES

The biomass processing system of FIG. 1 includes a biogas plant. The biogas plant 10 ferments biomass and provides an aqueous mineral nutrient solution to an algae biomass growth container 20. Algae is grown in the algae growth container 20. The growth is promoted by the nutrient solution, carbon dioxide and sunlight.

When the algae is harvested, oil is extracted from the algae in the oil extraction processor 30. The remaining algae residue is charged into the pyrolysis reactor 40. In addition to the algae residue, the pyrolysis reactor is charged with lignocellulose-rich residue produced from the biogas plant and high or low ash biomass such as wood and grass.

The pyrolysis reactor pyrolyses the biomass mixture under intermediate pyrolysis conditions to form a mixture of solid char, ash, liquid vapours and gas. In one embodiment, the solid char is mixed with soil to form black earth at a biomass growth site. The gas and liquid vapour products are conveyed, at least in part, to a gasifier 50.

The gasifier 50 is additionally charged with low ash biomass wood. The mixture of biomass is gasified to produce syngas. The syngas is combusted in an engine 60 to produce electrical and thermal energy. Carbon dioxide from the gasifier and engine is conveyed through a pipe to the algae biomass growth container to promote the growth of algae.

As shown in FIG. 1, the solid products of the pyrolysis process (char and ash) may be washed using water. The resultant char wash is a nutrient-rich aqueous phase. This can be conveyed to the algae biomass growth container in order to promote algae growth.

As also shown in FIG. 1, the pyrolysis vapours may, in part, be diverted from the gasifier. In this case, the aqueous phase of the pyrolysis vapours may be conveyed to the algae biomass growth container as a nutrient-rich aqueous phase in order to promote algae growth.

The embodiments set out above have been described by way of example. Modifications of these embodiments, further embodiments and modifications thereof will be apparent to the skilled person on reading this disclosure and as such are within the scope of the invention.

The invention claimed is:

1. A biomass processing system having:
    an algae biomass growth container;
    a biomass pyrolysis apparatus for pyrolysis processing of biomass derived, at least in part, from the algae biomass growth container to produce pyrolysis products; and
    a pyrolysis product conveying apparatus linking the biomass pyrolysis apparatus and the biomass growth container for conveying at least part of at least one of said pyrolysis products from the biomass pyrolysis apparatus to the biomass growth container for promoting algae biomass growth;
    wherein the system is configured to convey a nutrient-rich aqueous phase produced directly or indirectly through pyrolysis processing to the biomass growth container, the system further including means for washing char produced through pyrolysis processing with water to produce the nutrient-rich aqueous phase.

2. The biomass processing system according to claim 1, wherein the system is configured to convey nitrogen-based fertiliser to the biomass growth container in addition to the nutrient-rich aqueous phase.

3. The biomass processing system according to claim 1, the system being configured such that the nutrient-rich aqueous phase conveyed to the biomass growth container has a greater concentration of phosphorus-based nutrients than nitrogen-based nutrients.

4. The biomass processing system according to claim 1, the system further including a gasifier for receiving the at least part of at least one of said pyrolysis products to produce gasification products.

5. The biomass processing system according to claim 4 wherein the system further includes a gasification product conveying apparatus linking the gasifier to the algae biomass growth container for conveying at least part of at least one of said gasification products from the gasifier to the algae biomass growth container.

6. A method of biomass processing including the steps:
growing algae biomass in an algae biomass growth container;
removing the algae biomass from said algae biomass growth container;
pyrolysing the algae biomass in a biomass pyrolysis apparatus to produce pyrolysis products that include char;
washing the char with water to produce a nutrient-rich aqueous phase; and
conveying with a pyrolysis product conveying apparatus at least part of at least one of said pyrolysis products from the biomass pyrolysis apparatus to the algae biomass growth container to promote algae biomass growth;
wherein the at least part of at least one of said pyrolysis products conveyed to the biomass growth container includes the nutrient-rich aqueous phase.

7. The method according to claim 6 further including the step of adding nitrogen-rich fertiliser to the biomass growth container in addition to the nutrient-rich aqueous phase.

8. The method according to claim 6, wherein the nutrient-rich aqueous phase has a greater concentration of phosphorus-based nutrients than nitrogen-based nutrients.

9. The method according to claim 6 further comprising the step of gasifying at least part of at least one of the pyrolysis products to produce gasification products.

10. The method according to claim 9 further comprising the step of conveying at least part of at least one of said gasification products from the gasifier to the algae biomass growth container.

* * * * *